(12) United States Patent
Biagetti et al.

(10) Patent No.: US 10,189,844 B2
(45) Date of Patent: Jan. 29, 2019

(54) PYRAZOLE DERIVATIVES AS PHOSPHOINOSITIDE 3-KINASES INHIBITORS

(71) Applicant: CHIESI FARMACEUTICI S.p.A., Parma (IT)

(72) Inventors: Matteo Biagetti, Parma (IT); Anna Maria Capelli, Parma (IT); Michele Retini, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

(21) Appl. No.: 15/420,513

(22) Filed: Jan. 31, 2017

(65) Prior Publication Data

US 2017/0226109 A1 Aug. 10, 2017

(30) Foreign Application Priority Data

Feb. 4, 2016 (EP) ..................................... 16154299

(51) Int. Cl.
| | | |
|---|---|---|
| *C07D 487/04* | (2006.01) | |
| *A61K 31/519* | (2006.01) | |
| *A61K 45/06* | (2006.01) | |

(52) U.S. Cl.
CPC .......... *C07D 487/04* (2013.01); *A61K 31/519* (2013.01); *A61K 45/06* (2013.01)

(58) Field of Classification Search
None
See application file for complete search history.

(56) References Cited

U.S. PATENT DOCUMENTS 9,527,869 B2 * 12/2016 Biagetti ............... C07D 519/00
2015/0353552 A1 12/2015 Achab et al.

FOREIGN PATENT DOCUMENTS

| WO | 2007/085556 | 8/2007 |
| WO | 2007/114926 | 10/2007 |

OTHER PUBLICATIONS

European Search Report in Application No. 16154299.8 dated May 9, 2016.
International Search Report in Application No. PCT/EP2017/052054 dated Apr. 6, 2017.
Fritz Eiden et al., "Archiv der Pharmazie" vol. 312, issue 10, Jan. 1, 1979, pp. 863-872.
Elena P. Mayoral et al., "Bioorganic & Medicinal Chemistry", vol. 11, No. 24, Dec. 1, 2003 (pp. 5555-5567).
O. S. Attaryan et al., "Russian Journal of General Chemistry", vol. 82, No. 10, Nov. 16, 2012, pp. 1724-1727.
Database Registry [Online] Chemical Abstracts Service, Columbus, Ohio, US; 2015 XP002756776, (2015).
Database Registry [Online] Chemical Abstracts Service, Columbus, Ohio, US; 2015 XP002756777, (2015).
Database Registry [Online] Chemical Abstracts Service, Columbus, Ohio, US; 2015 XP002756778, (2014).
Database Registry [Online] Chemical Abstracts Service, Columbus, Ohio, US; 2015 XP002756779, (2014).
Database Registry [Online] Chemical Abstracts Service, Columbus, Ohio, US; 2015 XP002756780, (2014).
Database Registry [Online] Chemical Abstracts Service, Columbus, Ohio, US; 2015 XP002756781, (2012).
Database Registry [Online] Chemical Abstracts Service, Columbus, Ohio, US; 2015 XP002756782, (2012).
Database Registry [Online] Chemical Abstracts Service, Columbus, Ohio, US; 2015 XP002756802, (2012).

* cited by examiner

*Primary Examiner* — Kamal A Saeed
(74) *Attorney, Agent, or Firm* — Oblon, McClelland, Maier & Neustadt, L.L.P.

(57) ABSTRACT

Compounds of formula (I) defined herein are phosphoinositide 3-kinases (PI3K) inhibitors and are useful for the treatment of disorders associated with PI3K enzymes.

19 Claims, No Drawings

PYRAZOLE DERIVATIVES AS PHOSPHOINOSITIDE 3-KINASES INHIBITORS

CROSS REFERENCES TO RELATED APPLICATIONS

This application claims priority to European Patent Application No. 16154299.8 filed on Feb. 4, 2016, which is incorporated herein by reference in its entirety.

BACKGROUND OF THE INVENTION

Field of the Invention

The present invention relates to compounds which inhibit phosphoinositide 3-kinases (hereinafter PI3K). In addition, the present invention relates to methods for the preparation of such a compound, pharmaceutical compositions which contain such a compound, and therapeutic uses of such a compound.

Discussion of the Background

In biochemistry, a kinase is a type of enzyme that transfers a phosphate group from a high-energy donor molecule, such as ATP, to a specific substrate, a process referred to as phosphorylation. Specifically, PI3K enzymes are lipid enzyme kinases that can phosphorylate phosphoinosides (PIs) at the 3'-hydroxyl group of the inositol ring (see Panayotou et al, Trends Cell Biol 2:358-60 (1992) which is incorporated herein by reference in its entirety). It is well known that PIs, localized in the plasma membranes, can act as second messengers in signaling cascades by docking proteins containing pleckstrin-homology (PH), FYVE, PX and other phospholipid-binding domains (see Vanhaesebroeck B et al, Annu. Rev. Biochem 70, 535-602, 2001; Katso R et al, Annu. Rev. Cell Dev. Biol. 17, 615-675, 2001, which are incorporated herein by reference in their entireties).

Therefore, PIs can act as second messengers in many cellular processes including signal transduction, regulation of membrane trafficking and transport, cytoskeleton organization, cell survival and death, and many other functions.

PIs may be bound to the lipid bilayer of the cell membrane via two fatty acids that are attached to the cytosolic inositol ring via a glycerol phosphate linker. PIs inositol ring can be phosphorylated by PI3K enzymes, leading to the regulation of cellular growth, survival and proliferation. For this reason, PIs phosphorylation by PI3K enzymes is one of the most relevant signal transduction events associated with mammalian cell surface receptor activation (see Cantley L C, Science 296, 1655-7, 2002; Vanhaesebroeck B et al, Annu. Rev. Biochem 70, 535-602, 2001, which are incorporated herein by reference in their entireties).

The PI3K enzymes have been divided into three classes: Class I PI3K, Class II PI3K and Class III PI3K, on the basis of sequence homology, structure, binding partners, mode of activation, and substrate preference (see Vanhaesebroeck B et al, Exp. Cell Res. 253(1), 239-54, 1999; and Leslie N R et al, Chem. Rev. 101(8), 2365-80, 2001, which are incorporated herein by reference in their entireties).

Class I PI3K convert phosphoinositide-(4,5)-diphosphate (PI(4,5)P2) to phosphoinositide-(3,4,5)-triphosphate (PI(3,4,5)P3), which functions as a second messenger. The signaling cascade activated by the increase in intracellular levels of PI(3,4,5)P3 is negatively regulated through the action of 5'-specific and 3'-specific phosphatases (see Vanhaesebroeck B et al., Trends Biochem. Sci. 22(7), 267-72, 1997; Katso R et al, Annu. Rev. Cell Dev. Biol. 17, 615-75, 2001; and Toker A, Cell. Mol. Life Sci. 59(5), 761-79, 2002, which are incorporated herein by reference in their entireties).

Class II PI3K enzymes are the most recently identified class of PI3K and their exact function is still unclear.

Class III PI3K enzymes consists of a single family member, which is structurally related to Class I PI3K enzymes and appears to be important in endocytosis and vesicular trafficking. However, there are some evidences showing that Class III PI3K may be relevant in immune cell processes, such as phagocytosis and Toll-like receptor (TLR) signalling.

Class I PI3K enzymes can be further divided in class IA and class IB on the basis of their activation mechanisms.

In more detail, Class IA PI3K enzymes comprises three closely related isoforms: PI3Kα, PI3Kβ, and PI3Kδ, while Class IB comprises only the PI3Kγ isoform. These enzymes are heterodimers composed of a catalytic subunit known as p110, with four types: alpha (α), beta (β), delta (δ), and gamma (γ) isoforms, constitutively associated with a regulatory subunit. The first two p110 isoforms (α and β) are ubiquitously expressed and involved in cellular differentiation and proliferation. Consequently, PI3Kα and PI3Kβ enzymes have been extensively studied as targets for the development of new chemotherapeutic agents.

Otherwise, p110δ and p110γ isoforms are mainly expressed in leukocytes and are important in the activation of the immune response, such as leukocytes migration, B and T cells activation and mast cells degranulation. Therefore, PI3Kδ and PI3Kγ isoforms are very relevant in inflammatory respiratory diseases and in cancer.

Presently, the inhibitor derivatives of PI3K enzymes known in the art could generally inhibit said isoforms (alpha α, beta β, delta δ, and gamma γ isoforms) and they could act on the individual roles played in various diseases by said specific isoforms.

Therefore, specific activity assays of Class IA inhibitors for one specific PI3Kα, PI3Kβ, PI3Kδ and PI3Kγ isoform over another have been extensively developed in order to discern the suitable profile for the treatment of disorders associated with PI3K enzymes mechanisms. Such disorders could, for example, include respiratory diseases selected from idiopathic chronic cough, cough-variant asthma, cough associated with thoracic tumour or lung cancer, viral or post-viral cough, upper airways cough syndrome (UACS) or post nasal drip cough, or cough associated with gastro-oesophageal reflux disease both acid and non-acid, asthma, chronic bronchitis, chronic obstructive pulmonary disease (COPD), interstitial lung disease, idiopathic pulmonary fibrosis (IPF), congestive heart disease, sarcoidosis, infections (such as whooping cough), viral infections including viral respiratory tract infections and viral exacerbation of respiratory diseases; non-viral respiratory infections including aspergillosis and leishmanisis; allergic diseases including allergic rhinitis and atopic dermatitis; autoimmune diseases including systemic lupus erythematous, rheumatoid arthritis and multiple sclerosis; inflammatory disorders including inflammatory bowel disease; cardiovascular diseases including thrombosis and atherosclerosis; hematologic malignancies; neurodegenerative diseases; pancreatitis; multi-organ failure; kidney diseases; platelet aggregation; cancer; sperm motility; transplantation rejection; graft rejection; lung injuries; pain including pain associated with rheumatoid arthritis or osteoarthritis, back pain, general inflammatory pain, post hepatic neuralgia, diabetic neuropathy, inflammatory neuropathic pain (trauma), trigeminal neuralgia and central pain; stroke and surgical brain injury.

In view of the number of pathological responses which are mediated by PI3K enzymes, there is a continuing need for inhibitors of PI3K enzymes which can be useful in the treatment of many disorders. Thus, the invention relates to novel inhibitors of PI3Kα, PI3Kβ, PI3Kδ and PI3Kγ isoforms of Class I PI3K enzymes that, for the above reasons, may often have therapeutically desirable characteristics.

SUMMARY OF THE INVENTION

Accordingly, it is one object of the present invention to provide novel compounds which inhibit phosphoinositide 3-kinases (hereinafter PI3K).

It is another object of the present invention to provide novel methods for the preparation of such a compound.

It is another object of the present invention to provide novel pharmaceutical compositions which contain such a compound.

It is another object of the present invention to provide novel therapeutic uses of such a compound These and other objects, which will become apparent during the following detailed description, have been achieved by the inventors' discovery of compounds of formula (I):

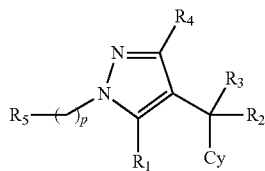

wherein $R_1$, $R_2$, $R_3$, $R_4$, $R_5$, Cy, and p are as described in the detailed description of the invention below, which act as inhibitors of phosphoinositide 3-kinases, processes for the preparation thereof, and pharmaceutical compositions comprising them either alone or in combination with one or more active ingredient, in admixture with one or more pharmaceutically acceptable carrier.

In one aspect, the present invention provides the use of a compound of the invention for the manufacture of a medicament.

In a further aspect, the present invention provides the use of a compound of the invention for the preparation of a medicament for the prevention and/or treatment of any disease characterized by phosphoinositide-3-kinase (PI3K) enzyme over-activity and/or wherein an inhibition of PI3K activity is desirable.

Moreover the present invention provides a method for prevention and/or treatment of any disease wherein a PI3K enzyme inhibition is desirable, said method comprising administering to a patient in need of such treatment a therapeutically effective amount of a compound of the invention.

In particular the compounds of the invention alone or combined with other active ingredients may be administered for the prevention and/or treatment of a disease of the respiratory tract characterized by inflammatory airway obstruction such as, for example, cough, asthma, COPD and IPF.

PI3K inhibitors are widely known as disclosed, for instance, in "PI3Kδ and PI3Kγ as Targets for Autoimmune and Inflammatory Diseases", Timothy D. Cushing, Daniela P. Metz, Douglas A. Whittington, and Lawrence R. McGee; Journal of Medicinal Chemistry 2012 55 (20), 8559-8581, which are incorporated herein by reference in their entireties. In addition, isocoumarines and indolizines derivatives are disclosed as PI3K inhibitors in WO 2015/091685 and WO 2015/193263 and pyridazinone derivatives in EP 14184586.7, all of which are incorporated herein by reference in their entireties.

The compounds of the present invention are inhibitors of the activity or function of the Class I of PI3K and more specifically, they are inhibitors of the activity or function of PI3Kα, PI3Kβ, PI3Kδ and/or PI3Kγ isoforms of the Class I PI3K.

Particularly, the compounds of the invention may have much more selectivity for the δ isoform of PI3K enzyme over other isoforms of the same enzyme.

Therefore, the compounds of the invention may be useful in the treatment of many disorders associated with PI3K enzymes mechanisms, such as respiratory diseases including asthma, chronic obstructive pulmonary disease (COPD), idiopathic pulmonary fibrosis (IPF) and cough; allergic diseases including allergic rhinitis and atopic dermatitis; autoimmune diseases including systemic lupus erythematous, rheumatoid arthritis and multiple sclerosis; inflammatory disorders including inflammatory bowel disease; cardiovascular diseases including thrombosis and atherosclerosis; hematologic malignancies; cystic fibrosis; neurodegenerative diseases; pancreatitis; multi-organ failure; kidney diseases; platelet aggregation; cancer; sperm motility; organ transplantation and in particular in transplant rejection; graft rejection; lung injuries; and pain including pain associated with rheumatoid arthritis or osteoarthritis, back pain, general inflammatory pain, post herpetic neuralgia, diabetic neuropathy, inflammatory neuropathic pain, trigeminal neuralgia, central pain, stroke and surgical brain injury.

DETAILED DESCRIPTION OF THE PREFERRED EMBODIMENTS

The invention is directed to a class of compounds acting as inhibitors of Phosphoinositide 3 Kinases (PI3K).

Said class of compounds inhibits the activity or function of the Class I of PI3K and more specifically, they are inhibitors derivatives of the activity or function of PI3Kα, PI3Kβ, PI3Kγ, and/or PI3Kδ isoforms of the Class I PI3K. The compounds of the present invention have the following formula (I):

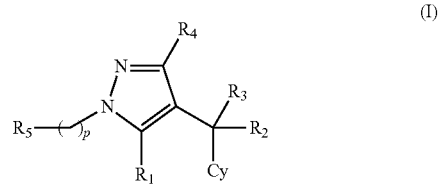

wherein
$R_1$ and $R_4$ and $R_5$ may be the same or different and are independently selected from the group consisting of: ($C_1$-$C_6$) alkyl, ($C_1$-$C_6$) haloalkyl, ($C_1$-$C_6$) hydroxyalkyl, ($C_1$-$C_6$) aminoalkyl and aryl optionally and independently substituted by one or more groups selected from halogen, —OH, —($CH_2$)$_p$$NR_6R_7$, —CN, ($C_1$-$C_6$) alkyl, ($C_1$-$C_6$) haloalkyl, ($C_1$-$C_6$) hydroxyalkyl, ($C_2$-$C_6$) alkenyl, ($C_2$-$C_6$) alkynyl, ($C_2$-$C_6$) hydroxyalkynyl;

$R_2$ is selected from H and $(C_1-C_6)$ alkyl;

$R_3$ is H;

Cy is a heteroaryl selected from the group consisting of I-1 to I-3 wherein (I-1) is purinyl, (I-2) is pyrazolo[3,4-d]pyrimidinyl, (I-3) is pyrimidinyl; each of which I-1 to I-3 can be optionally and independently substituted by one or more groups selected from halogen, —OH, —$(CH_2)_pNR_6R_7$, —CN, —CH═NOH, —$C(O)NR_6R_7$, —$C(O)OR_6$, $(C_1-C_6)$ alkyl, $(C_1-C_6)$ haloalkyl, $(C_1-C_6)$ hydroxyalkyl, $(C_1-C_6)$ alkanoyl, $(C_2-C_6)$ alkenyl, $(C_2-C_6)$ alkynyl, $(C_2-C_6)$ hydroxyalkynyl, aryl, heteroaryl and heterocycloalkyl, said aryl, heteroaryl, and heterocycloalkyl can be optionally and independently substituted with one or more groups selected from —OH, halogen, —CN, —$S(O)_2NR_6R_7$, —$NR_6S(O)_2R_7$, —$NR_6R_7$, $(C_1-C_6)$ alkyl, $(C_1-C_6)$ haloalkyl, $(C_1-C_6)$ hydroxyalkyl, $(C_1-C_6)$alkoxy;

$R_6$ and $R_7$ may have the same or different meanings at each occurrence, and are independently selected from the group consisting of —H and $(C_1-C_6)$ alkyl, $(C_1-C_6)$ haloalkyl, $(C_1-C_6)$ hydroxyalkyl, $(C_1-C_6)$ aminoalkyl, $(C_1-C_6)$ alkanoyl, and aryl $(C_1-C_6)$ alkanoyl or, when $R_6$ and $R_7$ are both linked to a nitrogen atom, they may form, taken together with the nitrogen atom they are linked to, a 4 to 6 membered heterocycle optionally containing one or more additional heteroatom or heteroatomic group selected from O, S, N, NH;

p is at each occurrence independently zero or an integer ranging from 1 to 3; or pharmaceutically acceptable salts and or solvates thereof.

Definitions

The term "pharmaceutically acceptable salts," as used herein, refers to derivatives of compounds of formula (I) wherein the parent compound is suitably modified by converting any of the free acid or basic group, if present, into the corresponding addition salt with any base or acid conventionally intended as being pharmaceutically acceptable.

Suitable examples of said salts may thus include mineral or organic acid addition salts of basic residues such as amino groups, as well as mineral or organic basic addition salts of acid residues such as carboxylic groups.

Cations of inorganic bases which can be suitably used to prepare salts according to the invention may comprise ions of alkali or alkaline earth metals such as potassium, sodium, calcium or magnesium or even ammonium salts.

The salts obtained by reacting a compound of formula (I) having a basic group with an inorganic or organic acid comprise for example, salts of hydrochloric acid, hydrobromic acid, sulfuric acid, phosphoric acid, methane sulfonic acid, toluene sulfonic acid, camphor sulfonic acid, acetic acid, oxalic acid, maleic acid, fumaric acid, succinic acid and citric acid.

Likewise, the compounds of the invention bearing acidic or basic groups can be suitably salified as above reported with amino acids.

In the present description, unless otherwise provided, the term "halogen" or "halogen atom" includes fluorine, chlorine, bromine and iodine, preferably chlorine or fluorine.

The term "$(C_1-C_6)$ alkyl" refers to straight-chained or branched-chained alkyl groups wherein the number of constituent carbon atoms is in the range 1 to 6. Particularly preferred alkyl groups are methyl, ethyl, n-propyl, isopropyl and t-butyl.

The expression "$(C_1-C_6)$ haloalkyl" refer to the above defined "$(C_1-C_6)$ alkyl" groups wherein one or more hydrogen atoms are replaced by one or more halogen atoms, which can be the same or different from each other.

Examples of said $(C_1-C_6)$ haloalkyl groups may thus include halogenated, poly-halogenated and fully halogenated alkyl groups wherein, in these latter, all of the hydrogen atoms are replaced by halogen atoms. Preferred examples of $(C_1-C_6)$ haloalkyl groups may be thus represented by trifluoromethyl or difluoro methyl groups.

By way of analogy, the terms "$(C_1-C_6)$ hydroxyalkyl" or "$(C_1-C_6)$ aminoalkyl" refer to the above defined "$(C_1-C_6)$ alkyl" groups wherein one or more hydrogen atoms are replaced by one or more hydroxy or amino group respectively.

The term "$(C_3-C_7)$ cycloalkyl" refers to saturated cyclic hydrocarbon groups containing 3 to 7 ring carbon atoms such as, for instance, cyclopropyl, cyclobutyl, cyclopentyl, cyclohexyl and cycloheptyl.

The term "$(C_2-C_6)$ alkenyl" refers to straight or branched carbon chains with one or more double bonds, conjugated or not conjugated, in cis or trans configuration, wherein the number of carbon atoms is 2 to 6.

By way of analogy, the term "$(C_5-C_7)$ cycloalkenyl" refers to cyclic hydrocarbon groups containing from 5 to 7 ring carbon atoms and one or two double bonds.

The term "$(C_2-C_6)$ alkynyl" refers to straight or branched carbon chains with one or more triple bonds wherein the number of carbon atoms is 2 to 6.

Likewise, the expression $(C_2-C_6)$ hydroxyalkynyl refers to the above alkynyl moieties wherein one or more hydrogen atoms are replaced by one or more hydroxyl groups.

The expression "aryl" refers to mono, bi- or tri-cyclic carbon ring systems which have 6 to 20, preferably 6 to 15 ring atoms, wherein at least one ring is aromatic. The expression "heteroaryl" refers to mono-, bi- or tri-cyclic ring systems with 5 to 20, preferably 5 to 15 ring atoms, in which at least one ring is aromatic and in which at least one ring atom is a heteroatom or heteroaromatic group (e.g. N, NH, S or O).

Examples of suitable aryl or heteroaryl monocyclic ring systems include phenyl, thienyl, pyrrolyl, pyrazolyl, imidazolyl, isoxazolyl, oxazolyl, isothiazolyl, thiazolyl, pyridinyl, pyrimidinyl, pyrazinyl, triazinyl, furanyl groups and the like.

Examples of suitable aryl or heteroaryl bicyclic ring systems include naphthalenyl, biphenyl-yl, purinyl, pteridinyl, pyrazolopyrimidinyl, benzotriazolyl, quinolinyl, isoquinolinyl, indolyl, isoindolyl, benzothiophenyl, benzodioxinyl, dihydrobenzodioxinyl, indenyl, dihydro-indenyl, dihydrobenzodioxepinyl, benzooxazinyl groups and the like.

Examples of suitable aryl or heteroaryl tricyclic ring systems include fluorenyl as well as benzocondensed derivatives of the aforementioned heteroaryl bicyclic ring systems.

The expression "heterocycloalkyl" refers to saturated or partially unsaturated monocyclic cycloalkyl groups in which at least one ring carbon atom is replaced by at least one heteroatom or hetero-group (e.g. N, NH, S or O). Particularly preferred are "$(C_3-C_6)$ heterocycloalkyl" referring to monocyclic cycloalkyl groups which have 3 to 6 ring atoms in which at least one ring carbon atom is replaced by at least one heteroatom or hetero-group. Examples of $(C_3-C_6)$ heterocycloalkyl are represented by: pyrrolidinyl, imidazolidinyl, thiazolidinyl, piperazinyl, piperidinyl, morpholinyl, thiomorpholinyl, dihydro- or tetrahydro-pyridinyl, tetrahydropyranyl, pyranyl, 2H- or 4H-pyranyl, dihydro- or tetrahydrofuranyl, dihydroisoxazolyl groups and the like.

From all of the above, it is clear that any group or substituent being defined through a composite name has to be intended as construed from the moieties from which it derives. Therefore, by way of example, the term "aryl $(C_1-C_6)$ alkyl" refers to any $(C_1-C_6)$ alkyl group as above defined, further substituted by an aryl group or ring as above defined. Suitable examples of the above aryl $(C_1-C_6)$ alkyl groups may thus include phenylmethyl, better known as benzyl, phenylethyl or phenylpropyl.

The term "$(C_1-C_6)$ alkanoyl", refers to HC(O)— (i.e. formyl) or to alkylcarbonyl groups (e.g. $(C_1-C_6)$ alkylC(O)— wherein the group "alkyl" has the meanings above reported). Examples of $(C_1-C_6)$ alkanoyl may thus include formyl, acetyl, propanoyl, butanoyl, isobutyryl, and the like.

The term "$(C_1-C_6)$alkoxy" refers to a straight or branched hydrocarbon of from 1 to 6 carbon atoms, attached to the rest of the molecule through an oxygen bridge (e.g. alkyloxy groups). Suitable examples of $(C_1-C_6)$alkoxy groups may thus include methoxy, ethoxy, n-propoxy, isopropoxy, n-butoxy, and the like.

The term "aryl $(C_1-C_6)$ alkanoyl" refers to the above $(C_1-C_6)$alkanoyl groups wherein the alkyl moiety is further substituted by an aryl group, wherein aryl and alkyl have the meaning above defined. Examples are represented by benzoyl, phenylacetyl, phenylpropanoyl or phenylbutanoyl groups.

The expression "ring system" refers to mono- or bicyclic or tricyclic ring systems which may be saturated, partially unsaturated or unsaturated, such as aryl, $(C_3-C_7)$ cycloalkyl, $(C_3-C_6)$ heterocycloalkyl or heteroaryl.

A dash ("-") that is not between two letters or symbols is meant to represent the point of attachment for a substituent.

An oxo moiety is represented by (O) as an alternative to the other common representation, e.g. (=O). Thus, in terms of general formula, the carbonyl group is herein preferably represented as —C(O)— as an alternative to the other common representations such as —CO—, —(CO)— or —C(=O)—, In general the bracketed group is a lateral group, not included into the chain, and brackets are used, when deemed useful, to help distinguish linear chemical formulas; e.g. the sulfonyl group —SO$_2$— might be also represented as —S(O)$_2$— to distinguish, e.g., the sulfinic group —S(O)O—.

It will be apparent that compounds of formula (I) may contain one or more stereogenic centers, for instance as represented in formula (IA) by the carbon atom (*) with an asterisk, wherein $R_2$ and $R_3$ have different meanings, and therefore may exist as optical stereoisomers.

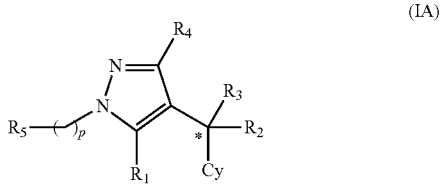

(IA)

Where the compounds according to the invention have at least one stereogenic center, they may accordingly exist as enantiomers. Where the compounds according to the invention possess two or more stereogenic centers, they may additionally exist as diastereoisomers. It is to be understood that all such single enantiomers, diastereoisomers and mixtures thereof in any proportion are encompassed within the scope of the present invention. The absolute configuration (R) or (S) for carbon (*) is assigned on the basis of Cahn-Ingold-Prelog nomenclature rules based on groups' priorities.

Atropisomers are stereoisomers resulting from hindered rotation about single bonds where the steric strain barrier to rotation is high enough to allow for the isolation of the conformers (see Bringmann G et al, Angew. Chemie Int. Ed. 44 (34), 5384-5427, 2005. doi:10.1002/anie.200462661, which is incorporated herein by reference in its entirety).

Oki defined atropisomers as conformers that interconvert with a half-life of more than 1000 seconds at a given temperature (see Oki M, Topics in Stereochemistry 14, 1-82, 1983, which is incorporated herein by reference in its entirety). Atropisomers differ from other chiral compounds in that in many cases they can be equilibrated thermally whereas in the other forms of chirality isomerization is usually only possible chemically.

Separation of atropisomers is possible by chiral resolution methods such as selective crystallization. In an atropoenantioselective or atroposelective synthesis one atropisomer is formed at the expense of the other. Atroposelective synthesis may be carried out by use of chiral auxiliaries like a Corey Bakshi Shibata (CBS) catalyst, an asymmetric catalyst derived from proline, or by approaches based on thermodynamic equilibration when an isomerization reaction favors one atropisomer over the other.

Racemic forms of compounds of formula (I) as well as the individual atropisomers if present (substantially free of its corresponding enantiomer) and stereoisomer-enriched atropisomers mixtures are included in the scope of the invention.

In a preferred embodiment, the present invention is directed to compounds of formula (I) as above defined wherein $R_2$ has the same meaning as above except H, $R_3$ is H and the absolute configuration of the chiral carbon (*) is (R).

In another embodiment the preferred configuration of the carbon (*) is (S).

In a preferred embodiment, the compounds of formula (I) are present as mixtures of enantiomers or diastereoisomers.

It is to be understood that all preferred groups or embodiments described herein below for compounds of formula (I) may be combined among each other and apply as well mutatis mutandis.

A first preferred group of compounds is that of formula (I) wherein:
$R_2$ is selected from H and $(C_1-C_6)$ alkyl;
$R_3$ is H;
Cy is a heteroaryl selected from the group consisting of I-1 to I-3 wherein (I-1) is 9H-purin-6-yl, (I-2) is 1H-pyrazolo[3,4-d]pyrimidin-1-yl, (I-3) is pyrimidin-4-yl; said I-1 to I-3 can be optionally substituted by one or more groups selected from halogen, —OH, —(CH$_2$)$_p$NR$_6$R$_7$, —CN, —CH=NOH, —C(O)NR$_6$R$_7$, —C(O)OR$_6$, $(C_1-C_6)$ alkyl, $(C_1-C_6)$ haloalkyl, $(C_1-C_6)$ hydroxyalkyl, $(C_1-C_6)$ alkanoyl, $(C_2-C_6)$ alkenyl, $(C_2-C_6)$ alkynyl, $(C_2-C_6)$ hydroxyalkynyl, aryl, heteroaryl and heterocycloalkyl; said aryl, heteroaryl and heterocycloalkyl can be optionally and independently substituted with one or more groups selected from —OH, halogen, —CN, —S(O)$_2$NR$_6$R$_7$, —NR$_6$S(O)$_2$R$_7$, —NR$_6$R$_7$, ($C_1$-$C_6$) alkyl, ($C_1$-$C_6$) haloalkyl, ($C_1$-$C_6$) hydroxyalkyl, ($C_1$-$C_6$)alkoxy; wherein all the other variables are as defined above;

or pharmaceutically acceptable salts or solvates thereof.

A class of preferred compounds of formula (I) is that wherein $R_1$ and $R_4$ and $R_5$ may be the same or different and are independently selected from the group consisting of: ($C_1$-$C_6$) alkyl which is methyl, and aryl which is phenyl;

$R_2$ is selected from H and ($C_1$-$C_6$) alkyl which is methyl;

$R_3$ is H;

Cy is a heteroaryl which is 1H-pyrazolo[3,4-d]pyrimidin-1-yl, substituted by one or more groups selected from —($CH_2$)$_p$$NR_6R_7$ which is —$NH_2$, aryl which is phenyl substituted with one or more groups selected from —OH and halogen which is fluorine;

p is in each occurrence independently 0 or 1;

or pharmaceutically acceptable salts and solvates thereof.

According to specific embodiments, the invention provides the compounds listed in the table below and pharmaceutical acceptable salts thereof.

| Example | Chemical name |
|---|---|
| Example 1 | 3-(4-amino-1-((1,3-dimethyl-5-phenyl-1H-pyrazol-4-yl)methyl)-1H-pyrazolo[3,4-d]pyrimidin-3-yl)-5-fluorophenol |
| Example 2 | 3-(4-amino-1-((1,5-dimethyl-3-phenyl-1H-pyrazol-4-yl)methyl)-1H-pyrazolo[3,4-d]pyrimidin-3-yl)-5-fluorophenol, |
| Example 3 | 3-(4-amino-1-(1-(1,3-dimethyl-5-phenyl-1H-pyrazol-4-yl)ethyl)-1H-pyrazolo[3,4-d]pyrimidin-3-yl)-5-fluorophenol, |
| Example 4 | 3-(4-amino-1-(1-(1,5-dimethyl-3-phenyl-1H-pyrazol-4-yl)ethyl)-1H-pyrazolo[3,4-d]pyrimidin-3-yl)-5-fluorophenol, |
| Example 5 | 3-(4-amino-1-((1-benzyl-3-methyl-5-phenyl-1H-pyrazol-4-yl)methyl)-1H-pyrazolo[3,4-d]pyrimidin-3-yl)-5-fluorophenol, |
| Example 6 | 3-(4-amino-1-((1-benzyl-5-methyl-3-phenyl-1H-pyrazol-4-yl)methyl)-1H-pyrazolo[3,4-d]pyrimidin-3-yl)-5-fluorophenol, |

The compounds of formula (I) including all the compounds here above listed can be generally prepared according to the procedure outlined in the following Schemes shown below using generally known methods.

Compounds of formula (II) may be prepared following the procedure described in Org. Lett, 2007, 9 (22), 4491-4494, which is incorporated herein by reference in its entirety.

According to Scheme 1, a compound of formula (III) may be prepared from a compound of formula (II) by N-Alkylation. Typical reaction conditions comprise reacting a compound of formula (II) with an alkylating agent like iodomethane or benzyl bromide, in the presence of a base like $K_2CO_3$ in a suitable polar aprotic solvent, such as DMF, at an appropriate temperature, such as, for example, at rt. (step 1)

According to Scheme 1, a compound of formula (IVa) where $R_2$=$R_3$=H may be prepared from compound of formula (III) by reduction. Typical reaction conditions comprise reacting a compound of formula (III) with a reducing agent like LiAlH$_4$, in a suitable polar aprotic solvent, such as THF, at an appropriate temperature, such as, for example, at 0° C. (step 2)

According to Scheme 1, a compound of formula (IVb) where $R_2$=H, $R_3$=Me may be prepared from compound of formula (IVa) by oxidation to compound (V) (step 3) followed by reaction with an organometallic reagent (step 4). Typical reaction conditions for oxidation (step 3) comprise reacting a compound of formula (IVa) with an oxidizing agent like manganese dioxide, in a suitable solvent, such as DCM, at an appropriate temperature, for example at 50° C. Typical reaction conditions for the addition step (step 4) comprise reacting a compound of formula (V) with an organometallic reagent like methylmagnesium bromide in a suitable solvent, such as THF, at an appropriate temperature, such as, for example, at 0° C.

A compound of general formula (I) may be prepared according to Scheme 1 by reaction of a compound of formula (IVa) where $R_2$=$R_3$=H or (IVb) where $R_2$=Me, $R_3$=H with a nitrogen based nucleophile CyH (VI), such as for example 3-iodo-1H-pyrazolo[3,4-d]pyrimidin-4-amine (step 5). Typical reaction conditions comprise reacting a compound of formula (IVa) or (IVb) with (VI), in a polar aprotic solvent, such as THF, in the presence of a dialkyl azodicarboxylate, such as DIAD, and a triaryl phosphine, such as triphenylphosphine, at an appropriate temperature, such as, for example, ranging from RT to 50° C.

Scheme 1

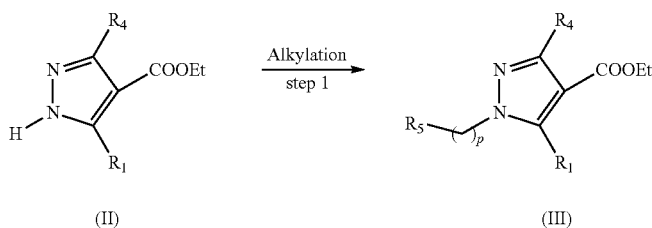

Reduction
step 2

-continued

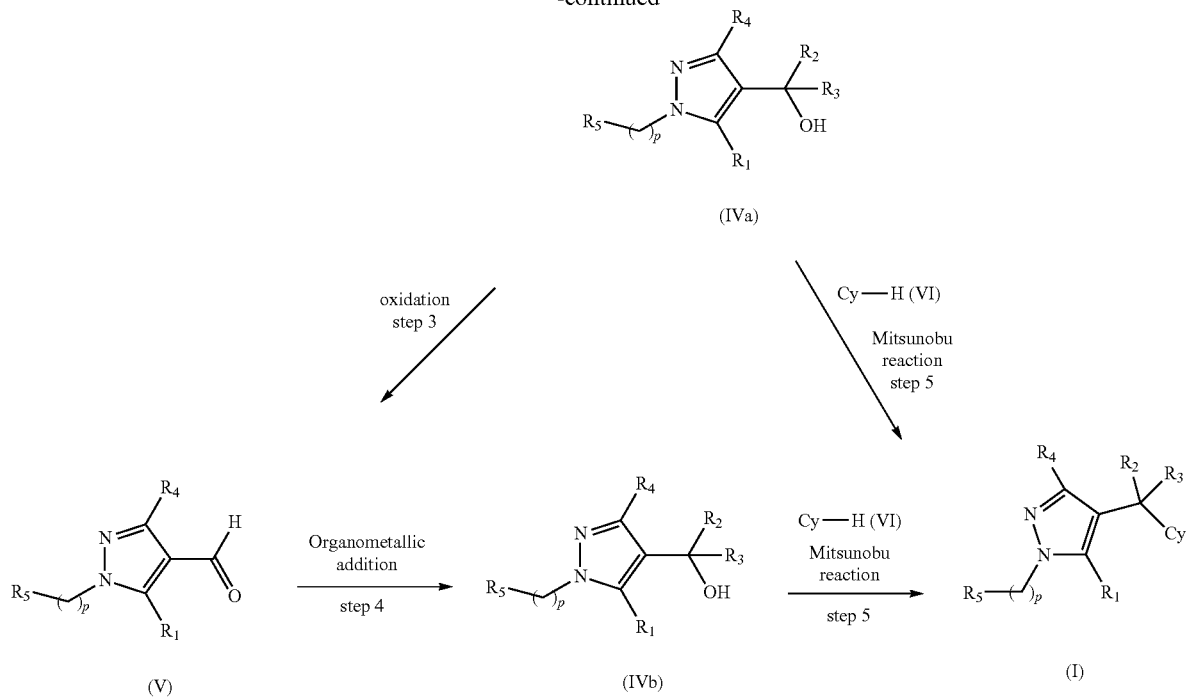

In the particular case when CyH (VI) is 3-iodo-1H-pyrazolo[3,4-d]pyrimidin-4-amine, the resulting compound of formula (I1), may be converted into compounds of formula (I2) according to Scheme 2 by means of a cross-coupling reaction, such as Suzuki cross-coupling with suitable reagents.

Scheme 2

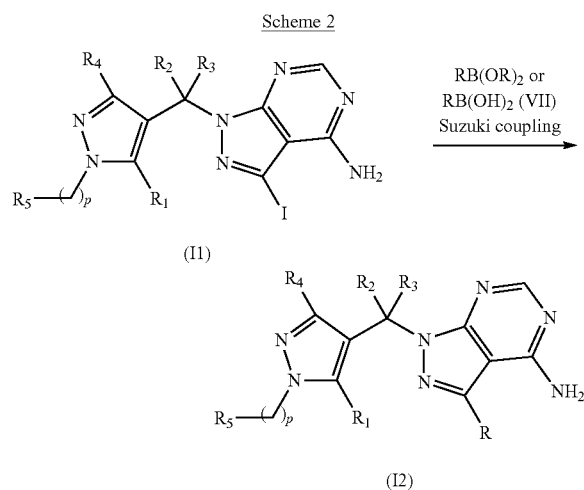

Typical Suzuki cross coupling conditions comprise reacting a compound of formula (I1) with a suitable boronic acid, or boronic ester (VII), in the presence of a Pd catalyst, such as Pd(PPh$_3$)$_4$, using a base, such as aqueous sodium bicarbonate, in a polar solvent or in a mixture of polar solvents, such as DME and EtOH, at an appropriate temperature, such as 80° C. An additional de-protection step could be required to remove protection group from OH or NH or NH$_2$ moieties.

The compounds of the present invention are inhibitors of kinase activity, in particular PI3-kinase activity. Generally speaking, compounds which are PI3K inhibitors may be useful in the treatment of many disorders associated with PI3K enzymes mechanisms.

In one embodiment, the disorders that can be treated by the compounds of the present invention include respiratory diseases selected from idiopathic chronic cough, cough-variant asthma, cough associated with thoracic tumour or lung cancer, viral or post-viral cough, upper airways cough syndrome (UACS), or post nasal drip cough, or cough associated with gastro-oesophageal reflux disease (both acid and non-acid reflux), asthma, chronic bronchitis, chronic obstructive pulmonary disease (COPD), interstitial lung disease, (such as idiopathic pulmonary fibrosis (IPF)), congestive heart disease, sarcoidosis, infections (such as whooping cough); viral infections (including viral respiratory tract infections and viral exacerbation of respiratory diseases; non-viral respiratory infections including aspergillosis and leishmaniosis; allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trauma), trigeminal neuralgia and central pain.

In another embodiment, the disorder that can be treated by the compound of the invention is selected from the group consisting of idiopathic chronic cough, cough-variant asthma, cough associated with thoracic tumour or lung cancer, viral or post-viral cough, upper airways cough syndrome (UACS), post nasal drip cough, cough associated gastro-oesophageal reflux disease (both acid and non-acid reflux), asthma, chronic bronchitis, chronic obstructive pulmonary disease (COPD) and interstitial lung disease (such as idiopathic pulmonary fibrosis (IPF)).

In a further embodiment, the disorder is selected from the group of asthma, chronic obstructive pulmonary disease (COPD), idiopathic pulmonary fibrosis (IPF), cough and chronic cough.

The methods of treatment of the present invention comprise administering a safe and effective amount of a compound of formula (I) or a pharmaceutically acceptable salt thereof to a patient in need thereof. As used herein, "safe and effective amount" in reference to a compound of formula (I) or a pharmaceutically acceptable salt thereof or other pharmaceutically-active agent means an amount of the compound sufficient to treat the patient's condition but low enough to avoid serious side effects and it can nevertheless be routinely determined by the skilled artisan. The compounds of formula (I) or pharmaceutically acceptable salts and or solvates thereof may be administered once or according to a dosing regimen wherein a number of doses are administered at varying intervals of time for a given period of time. Typical daily dosages may vary depending upon the particular route of administration chosen.

The present invention also provides pharmaceutical compositions of compounds of formula (I) in admixture with one or more pharmaceutically acceptable carrier or excipient, for example those described in Remington's Pharmaceutical Sciences Handbook, XVII Ed., Mack Pub., N.Y., U.S.A., which is incorporated herein by reference in its entirety.

Administration of the compounds of the invention may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and known excipients, including suspending agents, solubilizers, buffering agents, binders, disintegrants, preservatives, colorants, flavors, lubricants and the like. Time release capsules, tablets and gels are also advantageous in administering the compounds of the present invention.

Various liquid oral dosage forms can also be used for administering compounds of the invention, including aqueous and non-aqueous solutions, emulsions, suspensions, syrups, and elixirs. Such dosage forms can also contain suitable known inert diluents such as water and suitable known excipients such as preservatives, wetting agents, sweeteners, flavors, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the invention can be prepared by mixing the compound with a suitable excipient such as cocoa butter, salicylates and polyethylene glycols.

Formulations for vaginal administration can be in the form of cream, gel, paste, foam, or spray formula containing, in addition to the active ingredient, such as suitable carriers, are also known.

For topical administration the pharmaceutical composition can be in the form of creams, ointments, liniments, lotions, emulsions, suspensions, gels, solutions, pastes, powders, sprays, and drops suitable for administration to the skin, eye, ear or nose.

Topical administration may also involve transdermal administration via means such as transdermal patches.

For the treatment of the diseases of the respiratory tract, the compounds according to the invention are preferably administered by inhalation.

Inhalable preparations include inhalable powders, propellant-containing metering aerosols or propellant-free inhalable formulations.

For administration as a dry powder, single- or multi-dose inhalers known from the prior art may be utilized. In that case the powder may be filled in gelatin, plastic or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic nebulizers known from the prior art or by soft-mist nebulizers such as Respimat®.

The compounds of the invention can be administered as the sole active agent or in combination with other pharmaceutical active ingredients. Thus the present invention is also provides compositions comprising the compounds of formula I and/or pharmaceutically acceptable salts and solvates thereof, in combination with other pharmaceutical active ingredients including those currently used in the treatment of respiratory disorders, e.g. beta$_2$-agonists, antimuscarinic agents, corticosteroids, mitogen-activated kinases (P38 MAP kinases) inhibitors, human neutrophil elastase (HNE) inhibitors, phosphodiesterase 4 (PDE4) inhibitors, leukotriene modulators, non-steroidal anti-inflammatory agents (NSAIDs) and mucus regulators.

The dosages depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of formula (I) can be administered for example, at a dosage comprised between 0.001 and 1000 mg/day, preferably between 0.1 and 500 mg/day.

When the compounds of formula (I) are administered by the inhalation route, they are preferably given at a dosage comprised between 0.001 and 500 mg/day, preferably between 0.1 and 200 mg/day.

Other features of the invention will become apparent in the course of the following descriptions of exemplary embodiments which are given for illustration of the invention and are not intended to be limiting thereof.

EXAMPLES

Chemical Names of the compounds were generated with Cambridgesoft ChemBioDraw tool.
Abbreviations:

| | |
|---|---|
| EtOAc | Ethyl acetate |
| DCM | Dichloromethane |
| MeOH | Methanol |
| DMF | N,N-Dimethylformamide |
| MeCN | Acetonitrile |
| THF | Tetrahydrofuran |
| DMSO | Dimethyl sulfoxide |
| EtOH | Ethanol |
| DME | 1,2-Dimethoxyethane |
| Pd(PPh$_3$)$_4$ | Tetrakis(triphenylphosphine)palladium(0) |
| PPh$_3$ | Triphenylphosphine |
| DIAD | Diisopropyl azodicarboxylate |
| SCX | Strong cation exchanger |
| Silica-NH | Secondary amine functionalized silica cartridge |
| r.t./RT | Room temperature |
| Rt | Retention time |
| h | Hour |
| min | Minutes |
| conc | concentrated |
| eq | Equivalent |
| sat | Saturated |

General Experimental Details

Many of the compounds described in the following Examples have been prepared from stereochemically pure starting materials, for example 95% ee. Where the preparation of starting materials is not described, these are known, commercially available, or readily obtainable using standard procedures.

The stereochemistry of the compounds in the Examples, where indicated, has been assigned on the assumption that absolute configuration at resolved stereogenic centers of staring materials is maintained throughout any subsequent reaction conditions.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

Proton Magnetic Resonance ($^1$H NMR) spectra were collected using deuterated solvents (DMSO-d$_6$, CDCl$_3$ . . . etc) at 25° C. on Agilent VNMRS-500 and Bruker Avance 400. Chemical shifts are expressed in parts per million (ppm) downfield of tetramethylsilane (δ units). Multiplicity is indicated as follow: (s) singlet, (d) doublet, (dd) double doublet, (ddd) triple doublet, (t) triplet, (dt) double triplet, (q) quartet, (m) multiplet, (br s) broad signal. Coupling constants J are expressed in unit of hertz (Hz).

LCMS may be recorded under the following conditions: DAD chromatographic traces, mass chromatograms and mass spectra may be taken on UPLC/PDA/MS Acquity™ system coupled with Micromass ZQ™ or Waters SQD single quadrupole mass spectrometer operated in positive and/or negative ES ionisation mode and/or Fractionlynx system used in analytical mode coupled with ZQ™ single quadrupole operated in positive and/or negative ES ionisation mode.

QC methods operated under low pH conditions: column: Acquity CSH C18, 1.7 µm, 2.1×50 mm, the column temperature was 40° C.; mobile phase solvent A was milliQ water+0.1% HCOOH, mobile phase solvent B MeCN+0.1% HCOOH. The flow rate was 1 ml/min. The gradient table was t=0 min 97% A–3% B, t=1.5 min 0.1% A–99.9% B, t=1.9 min 0.1% A–99.9% B and t=2 min 97% A–3% B. The UV detection range was 210-350 nm and the ES+/ES− range was 100-1000 amu.

Flash chromatography purifications were performed using Biotage Isolera or Biotage SP 1 flash chromatography systems, both instruments working with Biotage silica cartridges and Biotage NH-cartridges, or were manually performed using Isolute Flash silica gel pre-packed cartridges, or Varian Bond Elut pre-packed cartridges.

SPE-SCX cartridges are ion exchange solid phase extraction columns supplied by Varian.

Brine refers to a saturated aqueous solution of NaCl. Unless otherwise specified, solutions of common inorganic salts used in workups are aqueous solutions.

Intermediate A1: ethyl 1,3-dimethyl-5-phenyl-1H-pyrazole-4-carboxylate and

Intermediate A2: ethyl 1,5-dimethyl-3-phenyl-1H-pyrazole-4-carboxylate

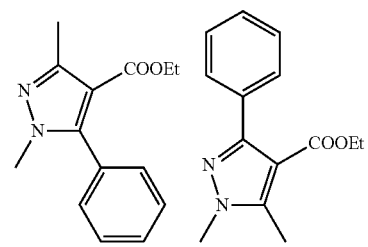

To a solution of ethyl 3-methyl-5-phenyl-1H-pyrazole-4-carboxylate, (prepared according to the procedure reported in Org. Lett, 2007, 9 (22), 4491-4494, which is incorporated herein by reference in its entirety) (0.570 g, 2.47 mmol) in DMF (30 ml), potassium carbonate (1.043 g, 7.42 mmol) was added followed by iodomethane (0.77 ml, 12.35 mmol) and the resulting mixture was stirred at RT for 2 hours. The mixture was diluted with ethyl acetate, filtered, and the resulting filtrate was washed with water and brine. The combined organic layers were dried over sodium sulfate and the solvent was removed. The residue was purified by flash chromatography on silica gel Biotage SNAP cartridge (eluting with cyclohexane:EtOAc=90:10 to 80:20) to afford as first eluting isomer intermediate A1, as a pale white solid (0.160 g). MS/ESI$^+$ 245.2, Rt=1.01 min.

It was also recovered as second eluting isomers, intermediate A2, as a pale white solid (0.2 g). MS/ESI$^+$ 245.2, Rt=0.99 min.

Intermediate A3: ethyl 1-benzyl-3-methyl-5-phenyl-1H-pyrazole-4-carboxylate and

Intermediate A4: ethyl 1-benzyl-5-methyl-3-phenyl-1H-pyrazole-4-carboxylate

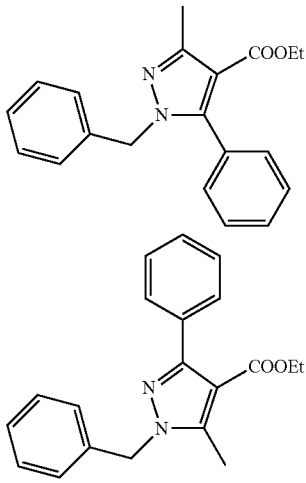

To a solution of ethyl 3-methyl-5-phenyl-1H-pyrazole-4-carboxylate, (prepared according to the procedure reported in Org. Lett, 2007, 9 (22), 4491-4494, which is incorporated herein by reference in its entirety) (0.530 g, 2.30 mmol) in DMF (28 ml), potassium carbonate (0.970 g, 6.90 mmol) was added followed by benzyl bromide (1.36 ml, 11.5 mmol) and the resulting mixture was stirred at RT for 2 hours. The mixture was diluted with ethyl acetate, filtered, washed with water and brine. The combined organic layers were dried over sodium sulfate and the solvent was removed. The residue was purified by flash chromatography on silica gel Biotage SNAP cartridge (cyclohexane:EtOAc=95:5 to 80:20) to afford as first eluting isomer intermediate A3 a pale white solid (0.297 g). MS/ESI$^+$ 321.0, Rt=1.23 min.

Intermediate A4 was also recovered, as second eluting isomers, as a pale white solid (0.120 g). MS/ESI$^+$ 321.0, Rt=1.22 min.

Intermediate B:
(1,3-dimethyl-5-phenyl-1H-pyrazol-4-yl)methanol

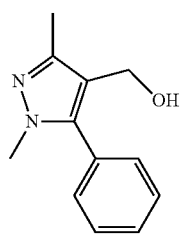

To a solution of ethyl 1,3-dimethyl-5-phenyl-1H-pyrazole-4-carboxylate A1 (0.140 g, 0.57 mmol) in THF (5.7 ml) at 0° C., 1M Lithium aluminum hydride in THF (1.14 ml) was added dropwise and the mixture was stirred at RT for 1 hour. The reaction was quenched with 15% aqueous NaOH at 0° C. The resulting mixture was extracted with diethyl ether and the combined organic layers were dried over sodium sulfate and the solvent was removed to afford the title compound as a pale white solid (0.112 g). MS/ESI$^+$ 203.1, Rt=0.65 min.

Intermediate B2:
(1,5-dimethyl-3-phenyl-1H-pyrazol-4-yl)methanol

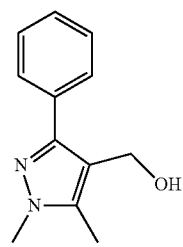

Prepared similarly to intermediate B1 starting from ethyl 1,5-dimethyl-3-phenyl-1H-pyrazole-4-carboxylate A2, (0.204 g, 0.83 mmol) to afford the title compound as a pale white solid (0.153 g).MS/ESI$^+$ 203.1, Rt=0.65 min.

Intermediate B3: (1-benzyl-3-methyl-5-phenyl-1H-pyrazol-4-yl)methanol

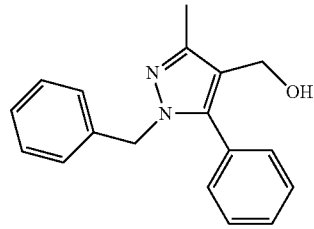 [SMILES: Cc1nn(Cc2ccccc2)c(-c2ccccc2)c1CO]

Prepared similarly to intermediate B1 starting from ethyl 1-benzyl-3-methyl-5-phenyl-1H-pyrazole-4-carboxylate A3 (0.150 g, 0.46 mmol) and purified by flash chromatography on silica gel Biotage cartridge (cyclohexane:EtOAc=80:20 to 50:50) to afford the title compound as a pale white solid (0.084 g). MS/ESI$^+$ 279.0, Rt=0.94 min.

Intermediate B4: (1-benzyl-5-methyl-3-phenyl-1H-pyrazol-4-yl)methanol

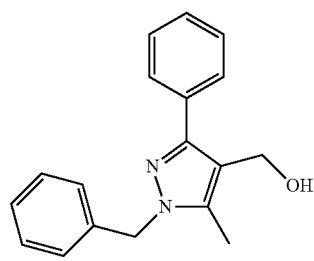 [SMILES: Cc1c(CO)c(-c2ccccc2)nn1Cc1ccccc1]

Prepared similarly to intermediate B1 starting from ethyl 1-benzyl-5-methyl-3-phenyl-1H-pyrazole-4-carboxylate A4 (0.120 g, 0.37 mmol) and purified by flash chromatography on silica gel Biotage cartridge (cyclohexane:EtOAc=80:20 to 50:50) to afford the title compound as a pale white solid (0.076 g). MS/ESI⁺ 279.0, Rt=0.90 min.

Intermediate C1:
1,3-dimethyl-5-phenyl-1H-pyrazole-4-carbaldehyde

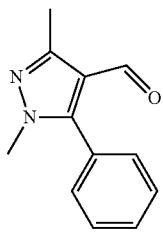

To a solution of compound (1,3-dimethyl-5-phenyl-1H-pyrazol-4-yl)methanol B1, (0.112 g, 0.55 mmol) in DCM (5 ml), manganese oxide (0.593 g, 6.6 mmol) was added and the mixture was heated at 50° C. for 6 hours. The mixture was diluted with DCM and filtered through a Celite® pad. The filtrate was evaporated to dryness to afford the title compound as a pale white solid (0.1 g). MS/ESI⁺ 201.1 [MH]⁺, Rt=0.82 min.

Intermediate C2:
1,5-dimethyl-3-phenyl-1H-pyrazole-4-carbaldehyde

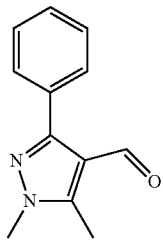

Prepared similarly to intermediate C1 starting from (1,5-dimethyl-3-phenyl-1H-pyrazol-4-yl)methanol B2, (0.153 g, 0.75 mmol) to afford the title compound as a pale white solid (150 mg). MS/ESI⁺ 201.1, Rt=0.82 min.

Intermediate D1: 1-(1,3-dimethyl-5-phenyl-1H-pyrazol-4-yl)ethan-1-ol

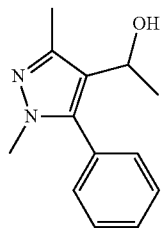 [SMILES: Cc1nn(C)c(-c2ccccc2)c1C(C)O]

To a solution of intermediate 1,3-dimethyl-5-phenyl-1H-pyrazole-4-carbaldehyde C1 (0.1 g, 0.5 mmol) in THF (5 ml) cooled at 0° C., 3M MeMgBr solution in Et₂O (0.25 mL, 0.75 mmol) was added drop-wise, and the resulting mixture was stirred at the same temperature for 15 minutes. The mixture was quenched with MeOH (1 ml), then diluted with EtOAc and washed with a mixture of sat. NH₄Cl and water. The aqueous phase was extracted with EtOAc and the combined organic layers were washed with brine, dried over sodium sulfate and the solvent was removed. The residue was purified by flash chromatography on Biotage silica-NH cartridge eluting with DCM to afford the title compound as a pale white solid (0.083 g). MS/ESI⁺ 217.2, Rt=0.72 min.

Intermediate D2: 1-(1,5-dimethyl-3-phenyl-1H-pyrazol-4-yl)ethan-1-ol

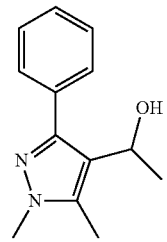 [SMILES: Cc1c(C(C)O)c(-c2ccccc2)nn1C]

Prepared similarly to intermediate D starting from 1,5-dimethyl-3-phenyl-1H-pyrazole-4-carbaldehyde C2 (0.150 g, 0.75 mmol) and purified by flash chromatography on Biotage silica-NH cartridge (cyclohexane:EtOAc=80:20 to 50:50) to afford the title compound as a pale white solid (0.107 g). MS/ESI⁺ 217.2, Rt=0.71 min.

Intermediate E1: 1-((1,3-dimethyl-5-phenyl-1H-pyrazol-4-yl)methyl)-3-iodo-1H-pyrazolo[3,4-d]pyrimidin-4-amine

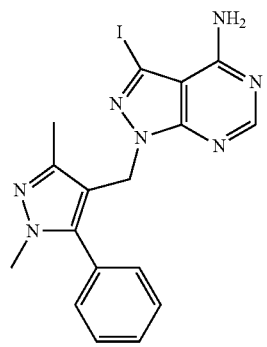 [SMILES: Cc1nn(C)c(-c2ccccc2)c1Cn1nc(I)c2c(N)ncnc21]

To a mixture of intermediate (1,3-dimethyl-5-phenyl-1H-pyrazol-4-yl)methanol B1, (0.058 g, 0.28 mmol), 3-iodo-1H-pyrazolo[3,4-d]pyrimidin-4-amine (0.089 g, 0.34 mmol) and PPh₃ (0.095 g, 0.36 mmol) in dry THF (5 ml), a solution of DIAD (0.067 ml, 0.34 mmol) in THF (1 ml) was added drop-wise at RT and left on stirring at that temperature overnight. The solvent was removed and the residue was purified by flash chromatography on Biotage silica-NH cartridge (cyclohexane:EtOAc=80:20 to 70:30) to afford the title compound (0.050 g). MS/ESI⁺ 446.2, Rt=0.78 min.

Intermediate E2: 1-((1,5-dimethyl-3-phenyl-1H-pyrazol-4-yl)methyl)-3-iodo-1H-pyrazolo[3,4-d]pyrimidin-4-amine

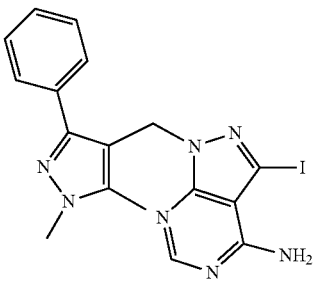 [SMILES: Cc1c(Cn2nc(I)c3c(N)ncnc32)c(-c2ccccc2)nn1C]

Prepared similarly to intermediate E1 starting from (1,5-dimethyl-3-phenyl-1H-pyrazol-4-yl)methanol B2 (0.075 g, 0.37 mmol) and purified by flash chromatography on Biotage silica-NH cartridge (cyclohexane:EtOAc=80:20 to 70:30) to afford the title compound (0.035 g). MS/ESI+ 446.2, Rt=0.79 min.

Intermediate E3: 1-(1-(1,3-dimethyl-5-phenyl-1H-pyrazol-4-yl)ethyl)-3-iodo-1H-pyrazolo[3,4-d]pyrimidin-4-amine

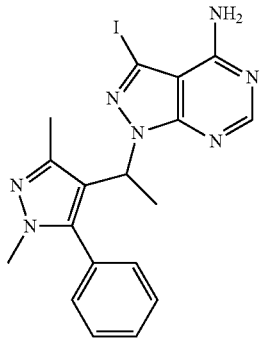 [SMILES: Cc1nn(C)c(-c2ccccc2)c1C(C)n1nc(I)c2c(N)ncnc21]

Prepared similarly to intermediate E1 starting from 1-(1,3-dimethyl-5-phenyl-1H-pyrazol-4-yl)ethan-1-ol D1 (0.083 g, 0.38 mmol) and purified by flash chromatography on Biotage silica-NH cartridge (cyclohexane:EtOAc=80:20 to 70:30) to afford crude title compound (0.050 g). This was used in the next step without any further purification. MS/ESI+ 460.3, Rt=0.84 min.

Intermediate E4: 1-(1-(1,5-dimethyl-3-phenyl-1H-pyrazol-4-yl)ethyl)-3-iodo-1H-pyrazolo[3,4-d]pyrimidin-4-amine

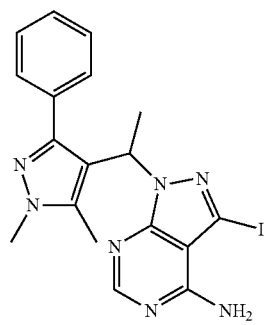 [SMILES: Cc1c(C(C)n2nc(I)c3c(N)ncnc32)c(-c2ccccc2)nn1C]

Prepared similarly to intermediate E1 starting from 1-(1,5-dimethyl-3-phenyl-1H-pyrazol-4-yl)ethan-1-ol D2 (0.107 g, 0.49 mmol) and purified by flash chromatography on Biotage silica-NH cartridge (cyclohexane:EtOAc=80:20 to 70:30) to afford crude title compound (0.080 g). This was used in the next step without any further purification. MS/ESI+ 460.0, Rt=0.83 min.

Intermediate E5: 1-((1-benzyl-3-methyl-5-phenyl-1H-pyrazol-4-yl)methyl)-3-iodo-1H-pyrazolo[3,4-d]pyrimidin-4-amine

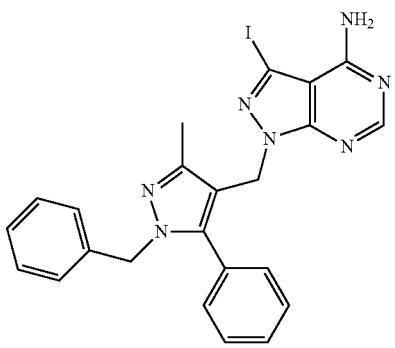 [SMILES: Cc1nn(Cc2ccccc2)c(-c2ccccc2)c1Cn1nc(I)c2c(N)ncnc21]

Prepared similarly to intermediate E1 starting from (1-benzyl-3-methyl-5-phenyl-1H-pyrazol-4-yl)methanol B3, (0.084 g, 0.30 mmol) and purified by flash chromatography on Biotage silica-NH cartridge (cyclohexane:EtOAc=70:30 to 50:50) to afford crude (0.044 g). This was used in the next step without any further purification. MS/ESI+ 522.0, Rt=1.03 min.

Intermediate E6: 1-((1-benzyl-5-methyl-3-phenyl-1H-pyrazol-4-yl)methyl)-3-iodo-1H-pyrazolo[3,4-d]pyrimidin-4-amine

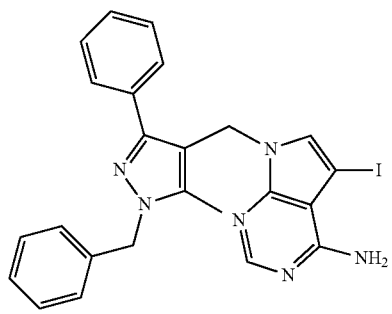 [SMILES: Cc1c(Cn2cc(I)c3c(N)ncnc32)c(-c2ccccc2)nn1Cc1ccccc1]

Prepared similarly to intermediate E1 starting from (1-benzyl-5-methyl-3-phenyl-1H-pyrazol-4-yl)methanol B4, (0.076 g, 0.27 mmol) and purified by flash chromatography on Biotage silica cartridge (cyclohexane:EtOAc=80:20 to 20:80). The resulting material was further purified by flash chromatography on Biotage silica-NH cartridge (DCM:MeOH=100:0 to 98:2) to afford the title compound (0.043 g). MS/ESI+ 522.0, Rt=0.98 min.

Example 1: 3-(4-amino-1-((1,3-dimethyl-5-phenyl-1H-pyrazol-4-yl)methyl)-1H-pyrazolo[3,4-d]pyrimidin-3-yl)-5-fluorophenol

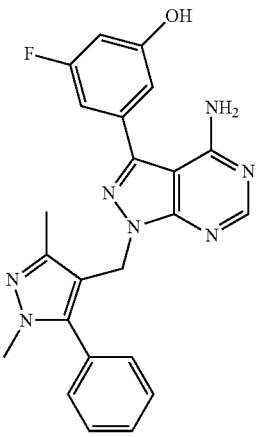 [SMILES: Cc1nn(C)c(-c2ccccc2)c1Cn1nc(-c2cc(O)cc(F)c2)c2c(N)ncnc21]

A mixture of 1-((1,3-dimethyl-5-phenyl-1H-pyrazol-4-yl)methyl)-3-iodo-1H-pyrazolo[3,4-d]pyrimidin-4-amine E1 (0.050 g, 0.11 mmol), (3-fluoro-5-hydroxyphenyl)boronic acid (0.019 g, 0.12 mmol) and Pd(PPh$_3$)$_4$ (6 mg, 0.005 mmol) in DME (11 ml), ethanol (1.65 ml) and saturated aqueous sodium carbonate (3.1 ml) was stirred at 80° C. overnight. The reaction was quenched by addition of water and extracted with DCM; the organic layer was dried over sodium sulfate, filtered and concentrated. The residue was purified by flash chromatography on Biotage silica-NH cartridge (DCM:MeOH=98:2 to 90:10) to afford title compound (14.2 mg). MS/ESI$^+$ 430.3 [MH]$^+$, Rt 0.77 min. $^1$H NMR (400 MHz, DMSO-d$_6$) δ ppm 10.17 (s, 1H), 8.23 (s, 1H), 7.45-7.55 (m, 5H), 6.85-6.90 (m, 1H), 6.77-6.83 (m, 1H), 6.66 (dt, 1H), 5.25 (s, 2H), 3.62 (s, 3H), 2.13 (s, 3H).

Example 2: 3-(4-amino-1-((1,5-dimethyl-3-phenyl-1H-pyrazol-4-yl)methyl)-1H-pyrazolo[3,4-d]pyrimidin-3-yl)-5-fluorophenol

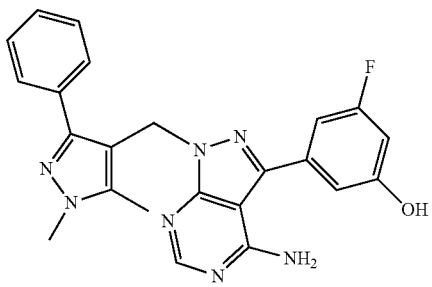 [SMILES: Cc1c(Cn2nc(-c3cc(O)cc(F)c3)c3c(N)ncnc32)c(-c2ccccc2)nn1C]

Prepared similarly to Example 1, starting from 1-((1,5-dimethyl-3-phenyl-1H-pyrazol-4-yl)methyl)-3-iodo-1H-pyrazolo[3,4-d]pyrimidin-4-amine E2, (0.035 g, 0.078 mmol), (3-fluoro-5-hydroxyphenyl)boronic acid (0.017 g, 0.11 mmol), Pd(PPh$_3$)$_4$ (4.5 mg, 0.0039 mmol) in DME (7.8 ml), ethanol (1.28 ml) and saturated aqueous sodium carbonate (2.2 ml), heating at 80° C. overnight. The crude was purified by flash chromatography on Biotage silica-NH gel cartridge (DCM:MeOH=98:2 to 90:10) to afford title compound (12.6 mg). MS/ESI$^+$ 430.3 [MH]$^+$, Rt 0.78 min. $^1$H NMR (400 MHz, DMSO-d$_6$) δ ppm 10.21 (br s, 1H), 8.31 (s, 1H), 7.77-7.85 (m, 2H), 7.29-7.43 (m, 3H), 6.84-6.88 (m, 1H), 6.75-6.80 (m, 1H), 6.61-6.68 (m, 1H), 5.45 (s, 2H), 3.77 (s, 3H), 2.33 (s, 3H).

Example 3: 3-(4-amino-1-(1-(1,3-dimethyl-5-phenyl-1H-pyrazol-4-yl)ethyl)-1H-pyrazolo[3,4-d]pyrimidin-3-yl)-5-fluorophenol

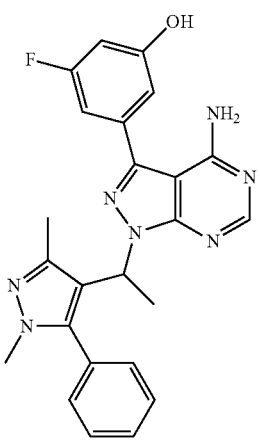 [SMILES: Cc1nn(C)c(-c2ccccc2)c1C(C)n1nc(-c2cc(O)cc(F)c2)c2c(N)ncnc21]

Prepared similarly to Example 1, starting from 1-(1-(1,3-dimethyl-5-phenyl-1H-pyrazol-4-yl)ethyl)-3-iodo-1H-pyrazolo[3,4-d]pyrimidin-4-amine E3, (0.050 g), (3-fluoro-5-hydroxyphenyl)boronic acid (0.022 g, 0.14 mmol), Pd(PPh$_3$)$_4$ (6.3 mg, 0.0055 mmol) in DME (11 ml), ethanol (1.65 ml) and sat. aqueous sodium carbonate (3.13 mL), heating at 80° C. overnight. The crude was purified by flash chromatography on Biotage silica-NH gel cartridge (DCM:MeOH=98:2 to 95:5) to afford title compound (5 mg). MS/ESI$^+$ 444.3 [MH]$^+$, Rt 0.79 min. $^1$H NMR (400 MHz, DMSO-d$_6$) δ ppm 10.22 (br s, 1H), 8.17 (s, 1H), 7.45-7.53 (m, 3H), 7.38-7.43 (m, 2H), 6.89-6.91 (m, 1H), 6.79-6.84 (m, 1H), 6.63-6.67 (m, 1H), 5.91 (q, 1H), 3.49 (s, 3H), 2.30 (s, 3H), 1.67 (d, 3H).

Example 4: 3-(4-amino-1-(1-(1,5-dimethyl-3-phenyl-1H-pyrazol-4-yl)ethyl)-1H-pyrazolo[3,4-d]pyrimidin-3-yl)-5-fluorophenol

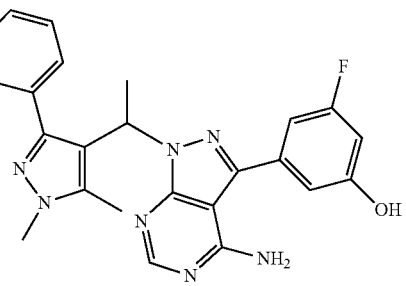

Prepared similarly to Example 1, starting from 1-(1-(1,5-dimethyl-3-phenyl-1H-pyrazol-4-yl)ethyl)-3-iodo-1H-pyrazolo[3,4-d]pyrimidin-4-amine E4, (0.080 g), (3-fluoro-5-hydroxyphenyl)boronic acid (0.033 g, 0.21 mmol), Pd(PPh$_3$)$_4$ (9.8 mg, 0.0085 mmol) in DME (17 ml), ethanol (2.78 ml) and saturated aqueous sodium carbonate (4.83 mL), heating at 80° C. for 5 hours. The crude was purified by flash chromatography on Biotage silica-NH gel cartridge (DCM:MeOH=98:2 to 90:10) to afford title compound (13.8 mg). MS/ESI$^+$ 444.1 [MH]$^+$, Rt 0.81 min. $^1$H NMR (400 MHz, DMSO-d$_6$) δ ppm 10.23 (br s, 1H), 8.24 (s, 1H), 7.60-7.64 (m, 2H), 7.34-7.43 (m, 3H), 6.93-6.95 (m, 1H), 6.85-6.89 (m, 1H), 6.68 (dt, 1H), 6.17 (q, 1H), 3.75 (s, 3H), 2.50 (s, 3H), 1.75 (d, 3H).

Example 5: 3-(4-amino-1-((1-benzyl-3-methyl-5-phenyl-1H-pyrazol-4-yl)methyl)-1H-pyrazolo[3,4-d]pyrimidin-3-yl)-5-fluorophenol

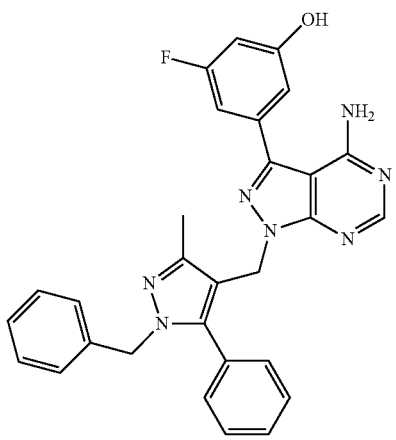 [SMILES: Cc1nn(Cc2ccccc2)c(-c2ccccc2)c1Cn1nc(-c2cc(O)cc(F)c2)c2c(N)ncnc21]

Prepared similarly to Example 1, starting from 1-((1-benzyl-3-methyl-5-phenyl-1H-pyrazol-4-yl)methyl)-3-iodo-1H-pyrazolo[3,4-d]pyrimidin-4-amine E5, (0.044 g), (3-fluoro-5-hydroxyphenyl)boronic acid (0.019 g, 0.12 mmol), Pd(PPh$_3$)$_4$ (4.85 mg, 0.0043 mmol) in DME (8.4 ml), ethanol (1.26 ml) and saturated aqueous sodium carbonate (2.4 mL), heating at 80° C. overnight. The crude was purified by flash chromatography on Biotage silica-NH gel cartridge (DCM:MeOH=98:2 to 95:5) to afford title compound (10.2 mg). MS/ESI$^+$ 506.3 [MH]$^+$, Rt 1.00 min. $^1$H NMR (400 MHz, DMSO-d$_6$) δ ppm 10.17 (br s, 1H), 8.28 (s, 1H), 7.77-7.83 (m, 2H), 7.31-7.40 (m, 5H), 7.24-7.28 (m, 1H), 7.14-7.19 (m, 2H), 6.84-6.87 (m, 1H), 6.74-6.78 (m, 1H), 6.64 (dt, 1H), 5.48 (s, 2H), 5.37 (s, 2H), 2.30 (s, 3H).

Example 6: 3-(4-amino-1-((1-benzyl-5-methyl-3-phenyl-1H-pyrazol-4-yl)methyl)-1H-pyrazolo[3,4-d]pyrimidin-3-yl)-5-fluorophenol

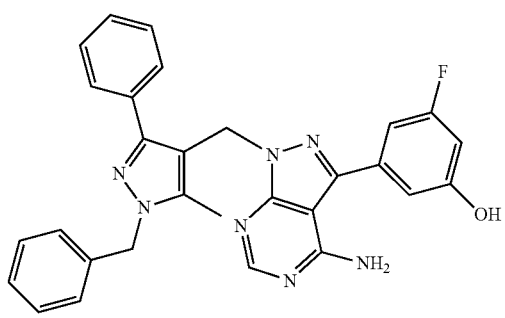 [SMILES: Cc1c(Cn2nc(-c3cc(O)cc(F)c3)c3c(N)ncnc32)c(-c2ccccc2)nn1Cc1ccccc1]

Prepared similarly to Example 1, starting from 1-((1-benzyl-5-methyl-3-phenyl-1H-pyrazol-4-yl)methyl)-3-iodo-1H-pyrazolo[3,4-d]pyrimidin-4-amine E6, (0.043 g, 0.082 mmol), (3-fluoro-5-hydroxyphenyl)boronic acid (0.019 g, 0.12 mmol), Pd(PPh$_3$)$_4$ (4.85 mg, 0.0043 mmol) in DME (8.4 ml), ethanol (1.26 mL) and saturated aqueous sodium carbonate (2.4 ml), heating at 80° C. overnight. The crude was purified by flash chromatography on Biotage silica-NH gel cartridge (DCM:MeOH=98:2 to 95:5) to afford title compound (9 mg). MS/ESI$^+$ 506.3 [MH]$^+$, Rt 0.96 min. $^1$H NMR (400 MHz, DMSO-d$_6$) δ ppm 10.18 (br s, 1H), 8.20 (s, 1H), 7.36-7.42 (m, 5H), 7.18-7.26 (m, 3H), 6.90-6.94 (m, 2H), 6.84-6.88 (m, 1H), 6.75-6.79 (m, 1H), 6.65 (dt, 1H), 5.25 (s, 2H), 5.10 (s, 2H), 2.14 (s, 3H).

Pharmacological Activity of the Compounds of the Invention.

In Vitro Determination of the PI3K Enzyme Inhibitory Activity in the Cell Free Assay Human recombinant proteins PI3Kα, PI3Kβ, PI3Kγ and PI3Kδ were purchased from Millipore Ltd (Billerica, Mass.). Compounds were dissolved at 0.5 mM in DMSO and were tested at different concentrations for their activity against PI3Ks using the ADP-Glo™ Kinase Assay (Promega, Madison Wis.) according to the manufacturer's instructions.

Briefly, the kinase reactions were performed in 384-well white plates (Greiner Bio-One GmbH, Frickenhausen). Each well was loaded with 0.1 µl of test compounds and 2.5 µl of 2× reaction buffer (40 mM Tris pH7.5, 0.5 mM EGTA, 0.5 mM Na$_3$VO$_4$, 5 mM β-glycerophosphate, 0.1 mg/ml BSA, 1 mM DTT), containing 50 µM PI and PS substrates (L-α-phosphatidylinositol sodium salt and L-α-phosphatidyl-L-serine, Sigma-Aldrich, St. Louis Mo.) and the PI3K recombinant proteins (PI3Kγ 0.25 ng/µl, PI3Kδ 1 ng/µl, PI3Kα 0.125 ng/µl, PI3Kβ 1 ng/µl).

The reactions were started by adding 2.5 µl of 2×ATP solution to each well (final concentrations: PI3Kγ ATP 3 µM; PI3Kδ ATP 80 µM; PI3Kα ATP 50 µM; PI3Kβ ATP 100 µM) and incubated for 60 minutes at room temperature. Subsequently, each kinase reaction was incubated for 40 minutes with 5 µl ADP-Glo™ Reagent, allowing depletion of unconsumed ATP. Then, the Kinase Detection Reagent (10 µl) was added in each well to convert ADP to ATP and to allow the newly synthesized ATP to be measured using a luciferase/luciferin reaction. Following a 60-minute incubation, the luminescence signal was measured using a Wallac EnVision® multilabel reader (PerkinElmer, Waltham Mass.).

Curve fitting and IC50 calculation were carried out using a four-parameter logistic model in XLfit (IDBS, Guilford, UK) for Microsoft Excel (Microsoft, Redmont, Wash.).

The compounds according to the invention showed IC50 lower than 1 µM in the PI3Kdelta inhibitory assay above described.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A compound of formula (I):

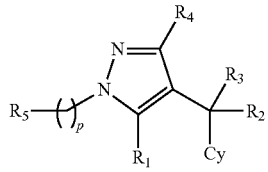

wherein:
R$_1$ and R$_4$ and R$_5$ may be the same or different and are each independently (C$_1$-C$_6$) alkyl, (C$_1$-C$_6$) haloalkyl, (C$_1$-C$_6$) hydroxyalkyl, (C$_1$-C$_6$) aminoalkyl, or aryl, each of which is optionally and independently substituted by one or more groups selected from the group consisting of halogen, —OH, —(CH$_2$)$_p$NR$_6$R$_7$, —CN, (C$_1$-C$_6$) alkyl, (C$_1$-C$_6$) haloalkyl, (C$_1$-C$_6$) hydroxyalkyl, (C$_2$-C$_6$) alkenyl, (C$_2$-C$_6$) alkynyl, and (C$_2$-C$_6$) hydroxyalkynyl;

R$_2$ is H or (C$_1$-C$_6$) alkyl;
R$_3$ is H;
Cy is a heteroaryl selected from the group consisting of I-1, I-2, and I-3 wherein I-1 is purinyl, I-2 is pyrazolo[3,4-d]pyrimidinyl, and I-3 is pyrimidinyl; each of which may be optionally and independently substituted by one or more groups selected from the group consisting of halogen, —OH, —(CH$_2$)$_p$NR$_6$R$_7$, —CN, —CH=NOH, —C(O)NR$_6$R$_7$, —C(O)OR$_6$, (C$_1$-C$_6$) alkyl, (C$_1$-C$_6$) haloalkyl, (C$_1$-C$_6$) hydroxyalkyl, (C$_1$-C$_6$) alkanoyl, (C$_2$-C$_6$) alkenyl, (C$_2$-C$_6$) alkynyl, (C$_2$-C$_6$) hydroxyalkynyl, aryl, heteroaryl, and heterocycloalkyl, wherein said aryl, heteroaryl, and heterocycloalkyl may be optionally and independently substituted with one or more groups selected from the group consisting of —OH, halogen, —CN, —S(O)$_2$NR$_6$R$_7$, —NR$_6$S(O)$_2$R$_7$, —NR$_6$R$_7$, (C$_1$-C$_6$) alkyl, (C$_1$-C$_6$) haloalkyl, (C$_1$-C$_6$) hydroxyalkyl, and (C$_1$-C$_6$)alkoxy;

R$_6$ and R$_7$ may be the same or different and are each independently —H and (C$_1$-C$_6$) alkyl, (C$_1$-C$_6$) haloalkyl, (C$_1$-C$_6$) hydroxyalkyl, (C$_1$-C$_6$) aminoalkyl, (C$_1$-C$_6$) alkanoyl, or aryl (C$_1$-C$_6$) alkanoyl or, when R$_6$ and R$_2$ are both linked to a nitrogen atom, they may form, taken together with the nitrogen atom to which they are linked, a 4 to 6 membered heterocycle optionally containing one or more additional heteroatom or heteroatomic group selected from the group consisting of O, S, N, and NH; and p is at each occurrence independently zero or an integer ranging from 1 to 3;
or a pharmaceutically acceptable salt thereof.

2. A compound or pharmaceutically acceptable salt according to claim 1, wherein:
R$_2$ is H or (C$_1$-C$_6$) alkyl;
R$_3$ is H; and
Cy is a heteroaryl selected from the group consisting of I-1, I-2, and I-3 wherein I-1 is 9H-purin-6-yl, I-2 is 1H-pyrazolo[3,4-d]pyrimidin-1-yl, and I-3 is pyrimidin-4-yl; each of which may be optionally substituted by one or more groups selected from the group consisting of halogen, —OH, —(CH$_2$)$_p$NR$_6$R$_7$, —CN, —CH=NOH, —C(O)NR$_6$R$_7$, —C(O)OR$_6$, (C$_1$-C$_6$) alkyl, (C$_1$-C$_6$) haloalkyl, (C$_1$-C$_6$) hydroxyalkyl, (C$_1$-C$_6$) alkanoyl, (C$_2$-C$_6$) alkenyl, (C$_2$-C$_6$) alkynyl, (C$_2$-C$_6$) hydroxyalkynyl, aryl, heteroaryl, and heterocycloalkyl, wherein said aryl, heteroaryl and heterocycloalkyl may be optionally and independently substituted with one or more groups selected from the group consisting of —OH, halogen, —CN, —S(O)$_2$NR$_6$R$_7$, —NR$_6$S(O)$_2$R$_7$, —NR$_6$R$_7$, (C$_1$-C$_6$) alkyl, (C$_1$-C$_6$) haloalkyl, (C$_1$-C$_6$) hydroxyalkyl, and (C$_1$-C$_6$)alkoxy.

3. A compound or pharmaceutically acceptable salt according to claim 1, wherein:
R$_1$ and R$_4$ and R$_5$ may be the same or different and are each independently methyl or phenyl;
R$_2$ is H or methyl;
R$_3$ is H;
Cy is 1H-pyrazolo[3,4-d]pyrimidin-1-yl, substituted by one or more groups selected from the group consisting of —NH$_2$ or phenyl, each of which may be substituted with one or more groups selected from the group consisting of —OH and fluorine; and
p is in each occurrence independently 0 or 1.

4. A compound or pharmaceutically acceptable salt according to claim 1, which is a compound selected from the group consisting of:
3-(4-amino-1-((1,3-dimethyl-5-phenyl-1H-pyrazol-4-yl)methyl)-1H-pyrazolo[3,4-d]pyrimidin-3-yl)-5-fluorophenol;
3-(4-amino-1-((1,5-dimethyl-3-phenyl-1H-pyrazol-4-yl)methyl)-1H-pyrazolo[3,4-d]pyrimidin-3-yl)-5-fluorophenol;
3-(4-amino-1-(1-(1,3-dimethyl-5-phenyl-1H-pyrazol-4-yl)ethyl)-1H-pyrazolo[3,4-d]pyrimidin-3-yl)-5-fluorophenol;
3-(4-amino-1-(1-(1,5-dimethyl-3-phenyl-1H-pyrazol-4-yl)ethyl)-1H-pyrazolo[3,4-d]pyrimidin-3-yl)-5-fluorophenol;
3-(4-amino-1-((1-benzyl-3-methyl-5-phenyl-1H-pyrazol-4-yl)methyl)-1H-pyrazolo[3,4-d]pyrimidin-3-yl)-5-fluorophenol; and
3-(4-amino-1-((1-benzyl-5-methyl-3-phenyl-1H-pyrazol-4-yl)methyl)-1H-pyrazolo[3,4-d]pyrimidin-3-yl)-5-fluorophenol,
or a pharmaceutical acceptable salt thereof.

5. A pharmaceutical composition, comprising a compound or pharmaceutically acceptable salt according to claim 1 and one or more pharmaceutically acceptable carrier or excipient.

6. A pharmaceutical composition, comprising a compound or pharmaceutically acceptable salt according to claim 2 and one or more pharmaceutically acceptable carrier or excipient.

7. A pharmaceutical composition, comprising a compound or pharmaceutically acceptable salt according to claim 3 and one or more pharmaceutically acceptable carrier or excipient.

8. A pharmaceutical composition, comprising a compound or pharmaceutically acceptable salt according to claim 4 and one or more pharmaceutically acceptable carrier or excipient.

9. A composition according to claim 5, further comprising one or more pharmaceutical active ingredient selected from the group consisting of a beta2-agonist, an antimuscarinic agent, a corticosteroid, a mitogen-activated kinase (P38 MAP kinase) inhibitor, a human neutrophil elastase (HNE) inhibitor, a phosphodiesterase 4 (PDE4) inhibitor, a leukotriene modulator, a non-steroidal anti-inflammatory agent (NSAID), and a mucus regulator.

10. A composition according to claim 6, further comprising one or more pharmaceutical active ingredient selected from the group consisting of a beta2-agonist, an antimuscarinic agent, a corticosteroid, a mitogen-activated kinase (P38 MAP kinase) inhibitor, a human neutrophil elastase (HNE) inhibitor, a phosphodiesterase 4 (PDE4) inhibitor, a leukotriene modulator, a non-steroidal anti-inflammatory agent (NSAID), and a mucus regulator.

11. A composition according to claim 7, further comprising one or more pharmaceutical active ingredient selected from the group consisting of a beta2-agonist, an antimuscarinic agent, a corticosteroid, a mitogen-activated kinase (P38 MAP kinase) inhibitor, a human neutrophil elastase (FINE) inhibitor, a phosphodiesterase 4 (PDE4) inhibitor, a leukotriene modulator, a non-steroidal anti-inflammatory agent (NSAID), and a mucus regulator.

12. A composition according to claim 8, further comprising one or more pharmaceutical active ingredient selected from the group consisting of a beta2-agonist, an antimuscarinic agent, a corticosteroid, a mitogen-activated kinase (P38 MAP kinase) inhibitor, a human neutrophil elastase (FINE) inhibitor, a phosphodiesterase 4 (PDE4) inhibitor, a leukotriene modulator, a non-steroidal anti-inflammatory agent (NSAID), and a mucus regulator.

13. A method for treating asthma, chronic obstructive pulmonary disease, or idiopathic pulmonary fibrosis, comprising administering to a subject in need thereof an effective amount of a compound or pharmaceutically acceptable salt according to claim 1.

14. A method for treating asthma, chronic obstructive pulmonary disease, or idiopathic pulmonary fibrosis, comprising administering to a subject in need thereof an effective amount of a compound or pharmaceutically acceptable salt according to claim 2.

15. A method for treating asthma, chronic obstructive pulmonary disease, or idiopathic pulmonary fibrosis, comprising administering to a subject in need thereof an effective amount of a compound or pharmaceutically acceptable salt according to claim 3.

16. A method for treating asthma, chronic obstructive pulmonary disease, or idiopathic pulmonary fibrosis, comprising administering to a subject in need thereof an effective amount of a compound or pharmaceutically acceptable salt according to claim 4.

17. A method for treating asthma, comprising administering to a subject in need thereof an effective amount of a compound or pharmaceutically acceptable salt according to claim 4.

18. A method for treating chronic obstructive pulmonary disease, comprising administering to a subject in need thereof an effective amount of a compound or pharmaceutically acceptable salt according to claim 4.

19. A method for treating idiopathic pulmonary fibrosis, comprising administering to a subject in need thereof an effective amount of a compound or pharmaceutically acceptable salt according to claim 4.

* * * * *